United States Patent

Fuchs et al.

[11] 4,316,994
[45] Feb. 23, 1982

[54] PREPARATION OF 4-FLUORO-3-PHENOXY-TOLUENE

[75] Inventors: Rainer Fuchs; Fritz Maurer, both of Wuppertal; Uwe Priesnitz, Unna-Massen; Hans-Jochem Riebel, Wuppertal, all of Fed. Rep. of Germany

[73] Assignee: Bayer Aktiengesellschaft, Leverkusen, Fed. Rep. of Germany

[21] Appl. No.: 170,194

[22] Filed: Jul. 18, 1980

[30] Foreign Application Priority Data

Aug. 8, 1979 [DE] Fed. Rep. of Germany ....... 2932093

[51] Int. Cl.³ .............................................. C07C 41/01
[52] U.S. Cl. .................................................... 568/639
[58] Field of Search ........................................ 568/639

[56] References Cited

FOREIGN PATENT DOCUMENTS 8734 3/1980 European Pat. Off. ............ 568/639
2242519 8/1972 Fed. Rep. of Germany.
2745006 10/1977 Fed. Rep. of Germany.

Primary Examiner—Bernard Helfin
Attorney, Agent, or Firm—Sprung, Felfe, Horn, Lynch & Kramer

[57] ABSTRACT

A process for the preparation of 4-fluoro-3-phenoxytoluene of the formula

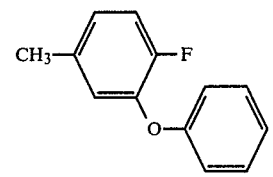

comprising reacting 3-bromo-4-fluoro-toluene of the formula

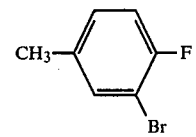

with an alkali metal or alkaline earth metal phenolate in the presence of copper as catalyst and in the presence if isoquinoline as diluent at a temperature between about 100° and 200° C. Advantageously the reaction is effected in the presence of about 0.9 to 1.5 mols of potassium or magnesium carbonate, about 1 to 1.2 mols of the phenolate, about 1 to 50 g of copper, copper(I) oxide, copper(I) chloride or copper (I) bromide as catalyst and about 150 to 1,500 ml of isoquinoline per mol of 3-bromo-4-fluoro-toluene.

8 Claims, No Drawings

PREPARATION OF 4-FLUORO-3-PHENOXY-TOLUENE

The invention relates to an unobvious process for the preparation of 4-fluoro-3-phenoxy-toluene.

It is known that in the reaction of fluoro-benzene derivatives which contain other halogen substituents, for example chlorine or bromine, in addition to fluorine, with alcoholates or phenolates, fluorine is replaced in preference to the other halogens.

Thus, for example, 4-chloro-diphenyl ether is formed as the main product from 4-fluoro-chlorobenzene and potassium phenolate (see DE-OS (German Published Specification) 2,169,489). The reaction of chloropentafluorobenzene with sodium pentafluorophenolate leads to an isomer mixture of 4-chloro-nonafluoro-diphenyl ether and 2-chloro-nonafluoro-diphenyl ether (see U.S. Pat. No. 3,637,866). Bromo-2,3,4,6-tetrafluorobenzene reacts with sodium methylate to give an isomer mixture of bromo-trifluoro-methoxy-benzenes (see J. Chem. Soc. Perkin II 1978, 137–141).

It is also known that diaryl ethers can be prepared from halogenoaromatic compounds and hydroxyaromatic compounds in the presence of copper or copper compounds as catalysts, but copper-catalyzed dehalogenation can in each case be observed as a side reaction (see J. Chem. Soc. 1965, 4,953).

The present invention now provides a process for the preparation of 4-fluoro-3-phenoxy-toluene, of the formula

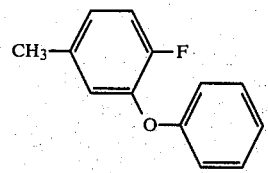
(I)

in which 3-bromo-4-fluoro-toluene, of the formula

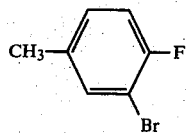
(II)

is reacted with an alkali metal phenolate or alkaline earth metal phenolate, if appropriate in the presence of an auxilliary selected from alkali metal carbonates and alkaline earth metal carbonates, and in the presence of copper or a copper compound as the catalyst, and in the presence of isoquinoline as the diluent, at a temperature between about 100° and 200° C.

It is surprising that virtually only 4-fluoro-3-phenoxytoluene is formed from 3-bromo-4-fluoro-toluene by the process according to the invention, since from the state of the art replacement of the fluorine with formation of 3-bromo-4-phenoxy-toluene was rather to be expected. It is likewise surprising that debromination to 4-fluorotoluene takes place to a far lesser extent than when the reaction is carried out by methods known from the literature.

The reaction according to the invention can be outlined by the following equation:

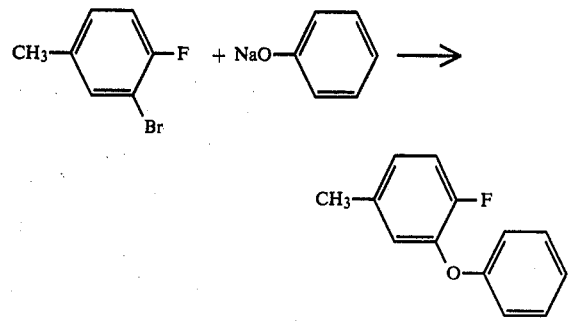

The 3-bromo-4-fluoro-toluene to be used as the starting compound is known (see Canad. Journ. Chem. 38 (1960), 2,441–2,449).

Examples of alkali metal phenolates or alkaline earth metal phenolates which can be used as starting substances are sodium phenolate, potassium phenolate or magnesium phenolate. Sodium phenolate is the preferred starting compound. Examples of auxiliaries from the alkali metal carbonate and alkaline earth metal carbonate series are potassium carbonate and magnesium carbonate. These auxiliaries are preferably used if sodium phenolate is employed as the starting compound.

Copper or copper compounds in various oxidation states are used as the catalysts. Examples which may be mentioned are copper, copper(I) oxide, copper(I) chloride and copper(I) bromide. Copper(I) oxide is preferably used.

The reaction temperature is kept between 100° and 200° C., preferably about 100° to 120° C. at the start of the reaction and then at about 140° to 180° C. until the end of the reaction.

1 to 1.5 mols, preferably 1 to 1.2 mols, of phenolate, 0.75 to 2 mols, preferably 0.9 to 1.5 mols, of an auxiliary from the alkali metal carbonate and alkaline earth metal carbonate series, 1 to 50 g of copper catalyst and 150 to 1,500 ml of isoquinoline are, in general, employed per mol of 3-bromo-4-fluoro-toluene.

In a preferred embodiment of the process according to the invention, 3-bromo-4-fluoro-toluene is initially introduced, together with the copper catalyst, into the isoquinoline and this mixture is heated to 100° to 120° C. The auxiliary and the phenolate are then added and the internal temperature is increased to about 160° C. The reaction mixture is stirred at this temperature until the reaction has ended. Working up can be carried out in the customary manner. For example, after cooling and filtering the mixture, the filtrate can be taken up in a water-immiscible solvent, for example cyclohexane, the solution can be washed with hydrochloric acid and water, dried and filtered and the solvent can be distilled off from the filtrate. The crude product which remains can be purified by vacuum distillation. Characterization is by the boiling point. High yields and good purity of the product can be achieved using the present invention.

4-Fluoro-3-phenoxy-toluene can be converted into 4-fluoro-3-phenoxy-benzyl bromide by reaction with N-bromosuccinimide in the presence of a free radical initiator, for example azodiisobutyronitrile, if appropriate using a diluent, for example carbon tetrachloride, at temperatures between 50° and 100° C. 4-Fluoro-3-phenoxy-benzyl bromide is known as an intermediate product for pesticides (see U.S. Pat. No. 4,218,469, issued Aug. 19, 1980).

EXAMPLE 1

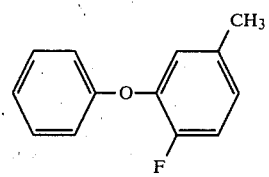

A mixture of 84.3 g of magnesium carbonate (4MgCO$_3$·Mg(OH)$_2$·4H$_2$O) and 128 g (1.1 mol) of sodium phenolate was added to a suspension of 189 g (1 mol) of 3-bromo-4-fluoro-toluene and 50 g of copper(I) oxide in 250 ml of isoquinoline at 110° C. The reaction temperature was then increased to 160° C. and the mixture was subsequently stirred at this temperature for 15 hours. Thereafter, the reaction mixture was cooled and filtered. The filtrate was taken up in cyclohexane. The cyclohexane solution was washed with hydrochloric acid and water, dried over sodium sulphate and then concentrated. After distillation of the residue, 170 g (84.1% of theory) of 4-fluoro-3-phenoxy-toluene were obtained in the form of a pale yellow oil of boiling point 105° C./6 mbars.

EXAMPLE 2

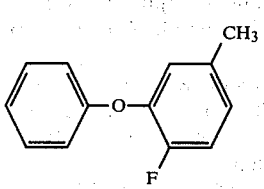

When 139 g (1 mol) of potassium carbonate were used instead of magnesium carbonate, 140 g (70% of theory) of 4-fluoro-3-phenoxy-toluene were obtained by the same method as described under Example 1.

EXAMPLE 3

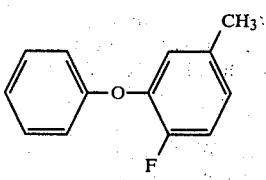

When the procedure was as in Example 1 and the reaction mixture was worked up by repeated fractional distillation, 141 g (70% of theory) of product were obtained in the form of a pale yellow oil of boiling point 105° C./6 mbars.

It will be appreciated that the instant specification and examples are set forth by way of illustration and not limitation, and that various modifications and changes may be made without departing from the spirit and scope of the present invention.

We claim:

1. In the preparation of 4-fluoro-3-phenoxy-toluene of the formula

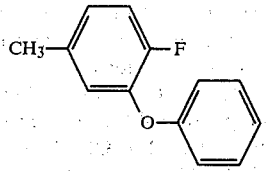

by reacting a 3-bromo-4-fluoro-toluene of the formula

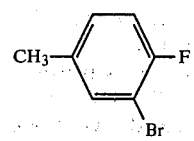

with an alkali metal or alkaline earth metal phenolate in the presence of copper as catalyst and in the presence of a diluent at a temperature between about 100° and 200° C., the improvement which comprises employing isoquinoline as the diluent and effecting the reaction in the presence of an alkali metal or alkaline earth metal carbonate.

2. A process according to claim 1, wherein the phenolate is sodium phenolate, potassium phenolate or magnesium phenolate.

3. A process according to claim 1, wherein the carbonate is potassium carbonate or magnesium carbonate.

4. A process according to claim 1, wherein the catalyst is copper, copper(I) oxide, copper(I) chloride or copper(I) bromide.

5. A process according to claim 1, wherein the reaction is effected initially at about 100° to 120° C. and subsequently at about 140° to 180° C.

6. A process according to claim 1, wherein about 1 to 1.5 mols of the phenolate, about 0.75 to 2 mols of the carbonate, about 1 to 50 g of the catalyst and about 150 to 1,500 ml of isoquinoline are employed per mol of 3-bromo-4-fluoro-toluene.

7. A process according to claim 6, wherein about 1 to 1.2 mols of the phenolate and about 0.9 to 1.5 moles of the carbonate are employed per mol of 3-bromo-4-fluoro-toluene.

8. A process according to claim 7, wherein the carbonate is potassium carbonate or magnesium carbonate, the catalyst is copper, copper(I) oxide, copper(I) chloride or copper(I) bromide, and the reaction is effected initially at about 100° to 120° C. and subsequently at about 140° to 180° C.

* * * * *

UNITED STATES PATENT AND TRADEMARK OFFICE
CERTIFICATE OF CORRECTION

PATENT NO. : 4,316,994
DATED : February 23, 1982
INVENTOR(S) : Rainer Fuchs et al.

It is certified that error appears in the above—identified patent and that said Letters Patent is hereby corrected as shown below:

Column 1, line 15, delete "2,169,489" and insert -- 2,619,489 --.

Signed and Sealed this

Twenty-second Day of June 1982

[SEAL]

Attest:

Attesting Officer

GERALD J. MOSSINGHOFF
Commissioner of Patents and Trademarks